(12) United States Patent
Chang et al.

(10) Patent No.: US 7,071,136 B2
(45) Date of Patent: Jul. 4, 2006

(54) ATTRITION RESISTANT MOLECULAR SIEVE CATALYSTS

(75) Inventors: Yun-Feng Chang, Houston, TX (US); Stephen N. Vaughn, Kingwood, TX (US); Luc R. M. Martens, Meise (BE); Kenneth R. Clem, Humble, TX (US)

(73) Assignee: ExxonMobil Chemical Patents Inc, Houston, TX (US)

( * ) Notice: Subject to any disclaimer, the term of this patent is extended or adjusted under 35 U.S.C. 154(b) by 146 days.

(21) Appl. No.: 10/442,586

(22) Filed: May 21, 2003

(65) Prior Publication Data

US 2004/0235649 A1    Nov. 25, 2004

(51) Int. Cl.
*B01J 29/06* (2006.01)
(52) U.S. Cl. .......................... 502/67; 502/64; 502/208; 502/214
(58) Field of Classification Search .................. 502/60, 502/64, 67, 208, 214
See application file for complete search history.

(56) References Cited

U.S. PATENT DOCUMENTS

| 3,816,342 | A | 6/1974 | Plank et al. ............. 252/455 Z |
| 6,153,552 | A | 11/2000 | Wachter et al. ............. 502/208 |
| 6,509,290 | B1 | 1/2003 | Vaughn et al. .............. 502/214 |
| 6,710,008 | B1 * | 3/2004 | Chang et al. ................ 502/214 |
| 2002/0016522 | A1 | 2/2002 | Vaughn et al. | |

FOREIGN PATENT DOCUMENTS

| WO | WO 03/000413 | 1/2003 |
| WO | WO 03/068395 | 8/2003 |

* cited by examiner

*Primary Examiner*—Christina Johnson

(57) ABSTRACT

This invention is directed to a hardened molecular sieve catalyst composition, a method of making the composition and a method of using the composition. The catalyst composition is made by mixing together molecular sieve, liquid, and an effective hardening amount of a dried molecular sieve catalyst to form a slurry. The slurry is dried, and then calcined to form the hardened molecular sieve catalyst composition. The hardened molecular sieve catalyst is highly attrition resistant.

13 Claims, 1 Drawing Sheet

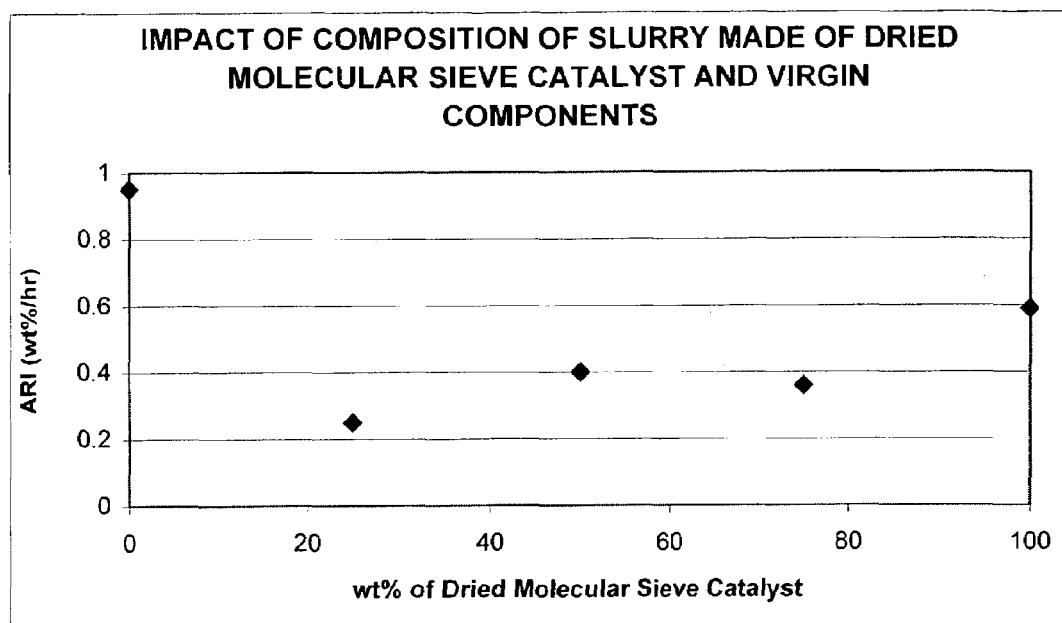
FIGURE

ATTRITION RESISTANT MOLECULAR SIEVE CATALYSTS

FIELD OF THE INVENTION

This invention relates to attrition resistant molecular sieve catalysts. In particular, this invention relates to attrition resistant molecular sieve catalysts that contain silicoaluminophosphate (SAPO) molecular sieve.

BACKGROUND OF THE INVENTION

A molecular sieve is generally a microporous structure composed of either crystalline aluminosilicate, belonging to a class of materials known as zeolites, or crystalline aluminophosphates, or crystalline silicoaluminophosphates. Molecular sieves can be made by hydrothermal crystallization from a reaction mixture comprising reactive sources of silicon and/or aluminum and/or phosphorous containing compounds, usually in the presence of one or several organic amines or quaternary ammonium salts as structure directing agents, also known as templates.

Molecular sieve catalysts are compositions made of molecular sieve particles bound together to form particles larger than the molecular sieve components. The molecular sieve catalyst particles can also include other components such as binders, fillers, like clay, and optionally other catalytically active agents such as rare earth metal oxides, transition metal oxides, or noble metal components.

Conventional methods of making molecular sieve catalyst particles include mixing together molecular sieve and binder, as well as other optional components such as fillers and other catalytic components. The mixture is typically stirred in solution to form a slurry, and the slurry is dried to form molecular sieve catalyst particles. Following drying, the particles are calcined to harden, as well as activate, the catalyst particles.

For example, U.S. Pat. No. 6,509,290 B1 (Vaughn et al.) discloses a method of making molecular sieve catalyst, the catalyst containing molecular sieve attrition particles and virgin molecular sieve. The attrition particles are essentially broken particles that have been recycled from a catalyst manufacture process or a reaction system. The method involves mixing together a molecular sieve, virgin binders and fillers, spray dried attrition particles or clumps, and non-virgin attrition particles from a reaction unit. The mixture is dried to form finished catalyst particles. To add strength to the finished catalyst particles, the attrition particles are substantially free of coke.

U.S. Pat. No. 6,153,552 (Wachter et al.) describes another method for making molecular sieve catalyst. The method involves mixing together a molecular sieve and an alumina sol, the alumina sol being made in solution and maintained at a pH of 2 to 10. The mixture is then spray dried and calcined. The calcined product is reported to be relatively hard, i.e., attrition resistant.

Certain catalytic reaction processes, particularly processes which convert oxygenates to olefins, require very hard molecular sieve catalyst compositions to survive the rigorous commercial scale reaction conditions over a relatively long period of time. Conventional methods of making molecular sieve catalysts fail to consistently achieve an appropriate hardness for effective commercial scale use. Additional methods are, therefore, needed for the manufacture of molecular sieve catalyst particles that are sufficiently hard to withstand rigorous commercial scale reaction conditions.

SUMMARY OF THE INVENTION

In one aspect, this invention provides a method for manufacturing molecular sieve catalyst particles that are sufficiently hard such that the catalyst can be used in commercial scale reaction systems for up to several months. Because the particles are of such hardness, they are strongly resistant to attrition, and can survive operations in systems such as fluidized bed systems. This is a particular advantage in riser reactor type fluidized bed systems, where the catalyst is circulated throughout the system at relatively high velocities and at relatively high temperatures. Because the particles are resistant to attrition, they can be left in the reaction system for extended periods of time.

In one aspect, this invention provides a method of making a hardened molecular sieve catalyst composition. In one embodiment, the method comprises mixing together molecular sieve, liquid, and an effective hardening amount of dried molecular sieve catalyst to form a slurry of solids and liquid. The slurry is dried, and the dried material is calcined to form the hardened molecular sieve catalyst composition.

In another embodiment, the invention provides a method, which comprises mixing together molecular sieve and dried molecular sieve catalyst to form a slurry of solids and liquid, wherein from 2 wt % to 98 wt % of the solids in the slurry, based on total weight of solids in the slurry, is dried molecular sieve catalyst. The slurry is dried, and the dried slurry is calcined to form the hardened molecular sieve catalyst composition.

In anther embodiment, the process comprises circulating a molecular sieve catalyst having an ARI of not greater than 0.6 wt %/hr through a reactor system for at least 4 months. During the process, the circulating molecular sieve catalyst is contacted with oxygenate to convert the oxygenate to olefin.

In one embodiment of the invention, binder, and optionally matrix material, are mixed with the molecular sieve and dried molecular sieve catalyst to form the slurry. Preferably, the binder is an inorganic oxide sol, more preferaby an alumina-containing sol. Preferably, the matrix material is clay.

The dried molecular sieve catalyst that is added to form the slurry acts to substantially increase the hardness or attrition resistance of the finished or calcined molecular sieve catalyst. Preferably, this finished or hardened molecular sieve catalyst has an ARI of not greater than 0.6 wt %/hr upon calcining, more preferably not greater than 0.5 wt %/hr upon calcining, and most preferably not greater than 0.4 wt %/hr upon calcining.

In one embodiment, from 2 wt % to 98 wt % of the solids in the slurry, based on total weight of solids in the slurry, is dried molecular sieve catalyst. Preferably, from 15 wt % to 80 wt % of the solids in the slurry, based on total weight of solids in the slurry, is dried molecular sieve catalyst. More preferably, from 20 wt % to 40 wt % of the solids in the slurry, based on total weight of solids in the slurry, is dried molecular sieve catalyst; and most preferably, from 20 wt % to 30 wt % of the solids in the slurry, based on total weight of solids in the slurry, is dried molecular sieve catalyst.

In another embodiment, from 10 wt % to 93 wt % of the solids in the slurry, based on total weight of solids in the slurry, is molecular sieve. Preferably, the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, metal containing molecular sieves thereof, and mixtures thereof. Also preferably, the dried molecular sieve catalyst contains molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, metal containing molecular sieves thereof, and mixtures thereof.

BRIEF DESCRIPTION OF THE DRAWING

An example of one embodiment of this invention is shown in the attached FIGURE, wherein the FIGURE shows the hardness effects of using dried molecular sieve catalyst as a slurry component in the manufacture of a final product catalyst.

DETAILED DESCRIPTION OF THE INVENTION

I. Hardened Molecular Sieve Catalyst

This invention is directed to hardened molecular sieve catalyst, methods of making the catalyst, and methods of using the catalyst. The molecular sieve catalyst is significantly harder than conventional molecular sieve catalysts, and can be used over an extended period of time, as it is highly resistant to attrition. For example, in fluidized bed systems, particularly fast fluidized bed systems, it is desirable to have hard catalysts so that they will not break apart due to forces encountered during operation, thus shortening useful catalyst life. It is particularly desirable in systems capable of converting oxygenates to olefins to be able to circulate catalyst throughout the catalyst system for up to at least 4, 6 or 8 months, perhaps longer, without encountering significant catalyst attrition. The catalyst of this invention can meet such rigorous requirements.

In one embodiment, the hardened molecular sieve catalyst is characterized according to an Attrition Rate Index (ARI). The ARI is used over other measurement methods, since many other methods are not sufficient to measure very highly attrition resistant molecular sieve catalysts, such as those made according to this invention.

The ARI methodology is similar to the conventional Davison Index method. The smaller the ARI, the more resistant to attrition; hence, the harder the catalyst. The ARI is measured by adding 6.0±0.1 g of catalyst, having a particle size ranging from 53 to 125 microns, into a hardened steel attrition cup. Approximately 23,700 scc/min of nitrogen gas is bubbled through a water-containing bubbler to humidify the nitrogen. The wet nitrogen is passed through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. Fines collected in the thimble are removed from the unit, and a new thimble installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in wt %/hr.

$$ARI=[C/(B+C)/D] \times 100\%$$

wherein
    B=weight of catalyst left in the cup after the attrition test;
    C=weight of collected fine catalyst particles after the first hour of attrition treatment; and
    D=duration of treatment in hours after the first hour attrition treatment.

The hardened molecular sieve catalyst of this invention has an ARI of not greater than about 0.6 wt %/hr. Preferably, the hardened molecular sieve catalyst has an ARI of not greater than about 0.5 wt %/hr, more preferably not greater than about 0.4 wt %/hr.

In one embodiment of the invention, the hardened molecular sieve catalyst has a particle size distribution such that not greater than about 10 wt % of the catalyst particles have an average diameter less than or equal to 20 μm. Preferably, the hardened molecular sieve catalyst has a particle size distribution such that not greater than about 5 wt % of the catalyst particles have an average diameter less than or equal to 20 μm; more preferably not greater than about 2 wt % of the catalyst particles have an average diameter less than or equal to 20 μm.

In another embodiment, the catalyst composition is comprised of catalyst particles in which not greater than about 10 wt % of the catalyst particles have an average diameter greater than or equal to about 250 μm. Preferably, not greater than about 5 wt % of the catalyst particles have an average diameter greater than or equal to about 250 μm; more preferably not greater than about 2 wt % of the catalyst particles have an average diameter greater than or equal to 250 μm.

In another embodiment of the invention, the hardened molecular sieve catalyst particles have a particle size distribution particularly suited for use in fluidized bed reaction systems. For example, in one embodiment, the hardened molecular sieve catalyst has a particle size distribution in μm of $2<d_{10}<50$; $30<d_{50}<120$; and $50<d_{90}<250$, wherein $d_{10}$ is the average diameter in which the cumulative volume of the sample reaches 10% of the total, $d_{50}$ is the average diameter in which the cumulative volume of the sample reaches 50% of the total, and $d_{90}$ is the average diameter in which the cumulative volume of the sample reaches 90% of the total. Preferably, the hardened molecular sieve catalyst has a particle size distribution in μm of $5<d_{10}<45$; $40<d_{50}<100$; and $70<d_{90}<200$; more preferably, a particle size distribution in μm of $10<d_{10}<40$; $50<d_{50}<100$; and $90<d_{90}<150$.

II. Method of Making the Hardened Molecular Sieve Catalyst

A. General Method of Making

The catalyst of this invention is manufactured by first mixing together various virgin catalyst components, liquid, and an effective hardening amount of a dried molecular sieve catalyst to form a slurry of solids and liquid. The slurry is then dried so as to form a hardened molecular sieve catalyst. The effective hardening amount of dried molecular catalyst is an amount that significantly enhances the hardness of a calcined final product catalyst (i.e., formulated molecular sieve catalyst).

B. Virgin Catalyst Components

According to this invention virgin catalyst components comprise any component materials conventionally used in the manufacture of formulated molecular sieve catalyst. Such components include molecular sieve, matrix material (including filler material and catalytically active components other than molecular sieve) and binder.

1. Molecular Sieves

Any molecular sieve, which has not been formulated into a catalyst composition, is included as one of the virgin catalyst components of this invention. Molecular sieves have various chemical, physical, and framework characteristics, and have been classified by the Structure Commission of the International Zeolite Association according to the rules of the IUPAC Commission on Zeolite Nomenclature. A framework-type describes the topology and connectivity of tetrahedrally coordinated atoms constituting the framework, and makes an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Crystalline molecular sieve materials all have a 3-dimensional, four-connected framework structure of corner-sharing $TO_4$ tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Small, medium and large pore molecular sieves have from a 4-ring to a 12-ring or greater framework-type. Typically, the molecular sieves employed herein have 8-, 10- or 12-ring structures and an average pore size in the range of from about 3 Å to 15 Å. More typically, the molecular sieves, preferably silicoaluminophosphate molecular sieves, have 8-rings and an average pore size less than about 5 Å, such as in the range of from 3 Å to about 5 Å, for example from 3 Å to about 4.5 Å, and particularly from 3.5 Å to about 4.2 Å.

Molecular sieves used herein have a molecular framework including at least [$AlO_4$] and [$PO_4$] tetrahedral units, such as aluminophosphates (AlPO), and typically including at least [$AlO_4$] and [$PO_4$] and [$SiO_4$] tetrahedral units, such as silicoaluminophosphates (SAPO). These silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [$QO_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in R. Szostak, *Handbook of Molecular Sieves*, Van Nostrand Reinhold, New York, N.Y. (1992), which is herein fully incorporated by reference.

The more preferred molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [$MeO_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements. Preferably M is selected from one of the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Where the molecular sieve is a silicoaluminophosphate or metal-containing silicoaluminophosphate, the SAPO typically has a Si/Al ratio less than 0.65, such as less than 0.40, for example less than 0.32, and particularly less than 0.20. In one embodiment the molecular sieve has a Si/Al ratio in the range of from about 0.65 to about 0.10, such as from about 0.40 to about 0.10, for example from about 0.32 to about 0.10, and particularly from about 0.32 to about 0.15.

Non-limiting examples of SAPO and AlPO molecular sieves useful herein are selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof. Of these, particularly useful molecular sieves are selected from the group consisting of SAPO-18, SAPO-34, SAPO-35, SAPO-44, SAPO-56, AlPO-18, AlPO-34, metal containing derivatives thereof, and mixtures thereof. More preferably the molecular sieves are selected from the group consisting of SAPO-18, SAPO-34, AlPO-34, AlPO-18, metal containing derivatives thereof, and mixtures thereof; and most preferably selected from the group consisting of SAPO-34, AlPO-18, metal containing derivatives thereof and mixtures thereof.

In one embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496 published Apr. 16, 1998, both of which are herein fully incorporated by reference. For example, SAPO-18, AlPO-18 and RUW-18 have an AEI framework-type, and SAPO-34 has a CHA framework-type. Thus the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

2. Matrix Materials

Matrix materials are optionally included in the slurry used to make the hardened molecular sieve catalyst of this invention. Such materials are typically effective as thermal sinks assisting in shielding heat from the catalyst composition, for example, during regeneration. They can further act to density the catalyst composition, increase catalyst strength such as crush strength and attrition resistance, and to control the rate of conversion in a particular process. Non-limiting examples of matrix materials include one or more of rare earth metals, metal oxides including titania, zirconia, magnesia, thoria, beryllia, quartz, silica or sols, and mixtures thereof; for example, silica-magnesia, silica-zirconia, silica-titania, silica-alumina and silica-alumina-thoria.

In one embodiment, matrix materials are natural clays, such as those from the families of montmorillonite and kaolin. These natural clays include kaolins known as, for example, Dixie, McNamee, Georgia and Florida clays. Non-limiting examples of other matrix materials include: halloysite, kaolinite, dickite, nacrite, or anauxite. Optionally, the matrix material, preferably any of the clays, are calcined, acid treated, and/or chemical treated before being used as a slurry component. Under the optional calcination treatment, the matrix material will still be considered virgin material as long as the material has not been previously used in a catalyst formulation.

In a particular embodiment, the matrix material is a clay or a clay-type composition, preferably a clay or clay-type composition having a low iron or titanium content, and most preferably the matrix material is kaolin. Kaolin has been found to form a pumpable, high solid content slurry; it has a low fresh surface area, and it packs together easily due to its platelet structure.

Preferably, the matrix material, particularly clay, and preferably kaolin, has an average particle size of from about 0.05 μm to about 0.75 μm; more preferably from about 0.1 μm to about 0.6 μm. It is also desirable that the matrix material have a $d_{90}$ particle size distribution of less than about 1.5 μm, preferably less than about 1 μm.

3. Binders

Binders are optionally included in the slurry used to make the hardened molecular sieve catalyst of this invention. Such materials act like glue, binding together the molecular sieve and other materials, to form a formulated catalyst composition. Non-limiting examples of binders include various types of inorganic oxide sols such as hydrated aluminas, silicas, and/or other inorganic oxide sols. In one embodiment of the invention, the binder is an alumina-containing sol, preferably aluminium chlorohydrate. Upon heating, the inorganic oxide sol, is converted into an inorganic oxide matrix component, which is particularly effective in forming a hardened molecular sieve catalyst composition. For example, an alumina sol will convert to an aluminium oxide matrix following heat treatment.

Aluminium chlorohydrate, a hydroxylated aluminium based sol containing a chloride counter ion, also known as aluminium chlorohydrol, has the general formula $Al_mO_n(OH)_oCl_p \cdot x(H_2O)$, wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., *Stud. Surf. Sci. and Catal.*, 76, pages 105–144, Elsevier, Amsterdam, 1993, which is herein incorporated by reference. In another embodiment, one or more binders are present in combination with one or more other non-limiting examples of alumina materials such as aluminium oxyhydroxide, γ-alumina, boehmite and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including silicon. In yet another embodiment, the binders are peptised alumina made by treating alumina hydrates such as pseudobohemite, with an acid, preferably a non-halogen acid, to prepare sols or aluminium ion solutions. Non-limiting examples of commercially available colloidal alumina sols include Nalco 8676 available from Nalco Chemical Co., Naperville, Ill., and Nyacol AL20DW available from the Nyacol Nano Technology Inc., Boston, Mass.

In one embodiment, the weight ratio of the binder to the molecular sieve is in the range of from about 0.1 to 0.5, such as in the range of from 0.1 to less than 0.5, for example in the range of from 0.11 to 0.48, conveniently from 0.12 to about 0.45, typically from 0.13 to less than 0.45, and particularly in the range of from 0.15 to about 0.4. In another embodiment, the weight ratio of the binder to the molecular sieve is in the range of from 0.11 to 0.45, such as in the range of from about 0.12 to less than 0.40, for example in the range of from 0.15 to about 0.35, and conveniently in the range of from 0.2 to about 0.3.

Where the catalyst composition contains a binder and a matrix omaterial, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material. It has been found that a higher sieve content and lower matrix content increases the molecular sieve catalyst composition performance, whereas a lower sieve content and higher matrix content improves the attrition resistance of the composition.

In general, the amount of binder and/or matrix material is such that the formulated molecular sieve catalyst composition contains from about 1% to about 99%, such as from about 10% to about 90%, such as from about 10% to about 80%, for example from about 20% to about 70%, and conveniently from about 25% to about 60% by weight of the molecular sieve based on the total weight of the molecular sieve catalyst composition.

C. Dried Molecular Sieve Catalyst Component

The dried molecular sieve catalyst component is made using the same virgin catalyst components described above (i.e., molecular sieve, and optionally matrix material and binder), and can be prepared according to conventional methods. For example, molecular sieve, optionally binder and/or matrix material, are mixed with a liquid to form a slurry. The slurry is then dried, preferably by spray drying, to form a dried molecular sieve catalyst. Since, the dried molecular sieve catalyst has not been calcined or used in any reaction process, it has not been activated, and is considered virgin material. The dried molecular sieve catalyst is then used as a catalyst component to form the hardened molecular sieve catalyst composition of this invention. Thus, the dried molecular sieve catalyst contains any one or more of the molecular sieves described above, and optionally any one or more of the matrix materials and/or binders described above.

If binder is not used in making the dried molecular sieve catalyst component, the dried molecular sieve catalyst is considered a dried binderless catalyst component, and can be used in making the hardened catalyst composition of this invention. If binder is used, the amount of binder used to prepare the dried molecular sieve catalyst component ranges from about 2% by weight to about 30% by weight, based on the total weight of the binder, the molecular sieve, and optionally included matrix material, excluding the liquid (i.e., after drying). Preferably the amount of binder used to prepare the dried molecular sieve catalyst ranges from about 5% by weight to about 20% by weight, more preferably from about 7% by weight to about 15% by weight, based on the total weight of the binder, the molecular sieve, and optionally included matrix material, excluding the liquid (i.e., after drying).

In one embodiment, the slurry used to make the dried molecular sieve catalyst component contains binder and matrix material at a weight ratio of from 0:1 to 1:1. Preferably, the slurry used to make the dried molecular sieve catalyst component contains binder and matrix material at a weight ratio of from 1:15 to 1:2, more preferably 1:10 to 1:2, and most preferably 1:6 to 1:1.

The liquid used to form the dried molecular sieve catalyst component can be any liquid conventionally used in formulating molecular sieve catalysts. Non-limiting examples of suitable liquids include water, alcohol, ketones, aldehydes, esters, or a combination thereof. Water is a preferred liquid.

The molecular sieve, and the optional matrix material and/or binder, used in making the dried catalyst component may be combined in the same or different liquid. Such components may be combined in any order, i.e., together, simultaneously, sequentially, or a combination thereof. In a preferred embodiment, the same liquid, preferably water, is used.

In one embodiment, a slurry of the molecular sieve, and optional binder and matrix materials, is mixed or milled to achieve a uniform slurry of sub-particles. The slurry is then fed to a forming unit that produces the dried molecular sieve catalyst composition. The forming unit may be any conventional unit, such as a spray dryer, pelletizer, extruder, granulator, etc. In a preferred embodiment, the forming unit is spray dryer. Typically, the forming unit is maintained at a temperature sufficient to remove a majority of the liquid from the slurry.

When a spray dryer is used as the forming (or drying) unit, typically, the slurry of the molecular sieve, and optional matrix material and/or binder, is co-fed to the spray drying volume with a drying gas. Conventional drying conditions can be used. Such conditions include an average inlet temperature ranging from about 150° C. to about 550° C., and an average outlet temperature ranging from about 100° C. to about 250° C.

During spray drying, the slurry is passed through a nozzle distributing the slurry into small droplets, resembling an aerosol spray, into a drying chamber. Atomization is achieved by forcing the slurry through a single nozzle or multiple nozzles with a pressure drop in the range of from about 100 psia to about 1,000 psia (about 690 kPaa to about 6,895 kPaa). In another embodiment, the slurry is co-fed through a single nozzle or multiple nozzles along with an atomization fluid such as air, steam, flue gas, or any other suitable gas.

In yet another embodiment, the slurry that is used to make the dried catalyst component is directed to the perimeter of a spinning wheel that distributes the slurry into small droplets. The size of the droplets is controlled by one or more factors including slurry viscosity, surface tension, flow rate, pressure, and temperature of the slurry; the shape and dimension of the nozzle(s); or the spinning rate of the wheel. These droplets are then dried in a co-current or counter-current flow of air passing through a spray dryer to form a partially, substantially or totally dried molecular sieve catalyst composition. An example of a conventional spray drying process is described in U.S. Pat. No. 4,946,814, which is incorporated herein by reference.

For purposes of this invention, dried means that the mixture used to form the dried molecular sieve catalyst has been heated in a drying or forming unit, but has not been calcined. Calcined catalysts are formed using a calcination process. The calcination process is considered a combustion process that takes place at a higher temperature than that of a drying process to combust or remove template from the molecular sieve component, or a pyrolysis or thermal decomposition process where the template molecules are disintegrated into volatile compounds.

Dried also means that at least a portion of the liquid used during the manufacture of the dried molecular sieve catalyst has been removed. The process of manufacturing the dried molecular sieve process is generally referred to as catalyst formulation, with the dried catalyst generally being referred to as formulated catalyst. The dried molecular sieve catalyst component optionally contains structure directing molecules (i.e., templates).

In an embodiment of the invention, the dried molecular sieve catalyst component contains template material. Template materials are chemical compounds that are added during the molecular sieve manufacturing process. During the formation of the molecular sieves themselves, a lattice type chemical structure is formed. This lattice type structure essentially wraps around the template material, with the template material acting as a means of forming a pore structure within the molecular sieve. The molecular sieve is ultimately formulated into a finished catalyst, and activated for catalytic use, by calcining or burning out the template. An elution process can also be used to remove the template, although calcination is preferred. Once the template is removed from the molecular sieve, a vast pore system remains within the molecular sieve structure. The pore system pore system is generally referred to as an intracrystalline pore system, and has active catalytic sites open to the immediate environment.

Since the drying conditions used in forming the dried molecular sieve catalyst component are less rigorous than the typical calcination conditions, the molecular sieve components of the dried molecular sieve catalyst preferably contains at least some of the original template material or at least a portion of a thermally degraded template. The remaining template or its thermal degradation product will typically be effective in covering active catalyst sites of the molecular sieve incorporated into the dried molecular sieve catalyst component. Because the active catalyst sites are generally covered by the template or a thermal degradation product of the template, the active sites are not available for catalytic activity, and the dried molecular sieve catalyst component is considered to be in the non-active form.

Representative templates which can be included in the first dried catalyst particles include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate.

D. Making a Slurry of Virgin Catalyst Components, Liquid and Dried Molecular Sieve Catalyst Virgin catalyst components, liquid, and dried molecular sieve are mixed together using conventional techniques to form a slurry. They are mixed in any order. For example, the virgin catalyst components and/or the dried molecular sieve catalyst can be added to the liquid, the liquid can be added to the virgin catalyst components or to the dried molecular sieve catalyst, and any remaining components can be subsequently added. The mixture is thoroughly stirred to form a slurry. The more thorough the stirring, the better the consistency of the slurry. In this case, the slurry is also called the final product slurry, since the final hardened catalyst will be made from this slurry.

In one embodiment of the invention, the dried molecular sieve catalyst is mixed with liquid to form a final product slurry. The liquid used to make this slurry is the same type of liquid used in making the dried molecular sieve catalyst component. Preferably, the liquid is water. The final product slurry optionally includes matrix material and binder as that used in making the slurry for forming the dried molecular sieve catalyst.

The mixing of the final product slurry is preferably sufficient to break larger dried molecular sieve catalyst particles included in the slurry. In general, the more vigorous the mixing, the smaller the dried molecular sieve catalyst particles formed in the slurry. Mixing using high-shear mixers is preferred. In general, high-shear mixers are capable of rotating at speeds of at least about 3,000 rpms laboratory scale equivalent.

Solids particle size of the slurry can be indirectly determined by measuring the viscosity of the slurry. In general, the higher the viscosity, the smaller the solids particle size in the slurry. The viscosity of the slurry should not be too high, so that mixing is not effective in breaking apart large particles, or too low, so that drying will not produce acceptable particle formation. Slurries having too high of a viscosity tend to cause problems in the spray dryer. For example, very high viscosity slurries tend to plug spray nozzles or spinning wheels used in spray dryers to form the spray dried materials. This plugging action can lead to the formation of irregularly shaped spray dried particles.

In one embodiment, the final product slurry has a viscosity of from about 100 cP (0.1 Pa/sec) to about 12,500 cP (12.5 Pa/sec), as measured using a Brookfield LV-DVE viscometer with a No. 3 spindle at 10 rpm. Preferably, the final product slurry has a viscosity of from about 200 cP (0.2 Pa/sec) to about 10,500 cP (10.5 Pa/sec), and more preferably from about 350 cP (0.375 Pa/sec) to about 10,000 cP (10 Pa/sec), as measured using a Brookfield LV-DVE viscometer with a No. 3 spindle at 10 rpm.

In another embodiment, the final product slurry has a solids content of from about 10 wt % to about 75 wt %, based on total weight of the slurry. Preferably the final product slurry has a solids content of from about 15 wt % to about 70 wt %, more preferably from about 20 wt % to about 65 wt %, based on the total weight of the slurry. The solids content can be measured using any conventional means. However, a CEM MAS 700 microwave muffle furnace is particularly preferred to give results consistent with the values recited herein.

The final product slurry contains sufficient dried molecular sieve catalyst to provide a hardened molecular sieve catalyst upon calcination. In one embodiment, the final product slurry contains from about 2 wt % to about 98 wt % dried molecular sieve catalyst, based on total weight of solids in the slurry. In another embodiment, the final product slurry contains from about 15 wt % to about 80 wt % dried molecular sieve catalyst, based on total weight of solids in the slurry. Preferably, the final product slurry contains from about 20 wt % to about 40 wt % dried molecular sieve catalyst, more preferably about 20 wt % to about 30 wt % dried molecular sieve catalyst, based on total weight of solids in the slurry.

The final product slurry also contains sufficient molecular sieve to be effective in its desired use. In one embodiment, the final product slurry contains from about 10 wt % to about 93 wt % molecular sieve, based on total weight of solids in the slurry. Preferably, the final product slurry contains from about 15 wt % to about 85 wt % molecular sieve, more preferably from about 20 wt % to about 80 wt % molecular sieve, based on total weight of solids in the slurry.

E. Drying and Hardening the Final Product Slurry

The final product slurry can be dried using any conventional drying method to form a hardened molecular sieve catalyst composition. In one embodiment, the final product slurry is spray dried to form a spray dried product, and the spray dried product is calcined. Calcination further hardens and/or activates the hardened molecular sieve catalyst composition. Calcination media useful in this invention include air, nitrogen, helium, flue gas (combustion product lean in oxygen), or any combination thereof. Air, optionally containing water, is a preferred type of calcination medium.

Conventional calcination temperatures can be used to form the hardened molecular sieve catalyst of this invention. Such temperatures are generally in the range from about 400° C. to about 1,000° C., preferably from about 500° C. to about 850° C., and most preferably from about 600° C. to about 800° C.

Conventional calcination devices can be used in this invention. Such devices include rotary calciners, fluid bed calciners, batch ovens, and the like. Calcination time is typically dependent on the degree of hardening of the molecular sieve catalyst composition and the temperature.

In one embodiment of the invention, a spray dried molecular sieve catalyst composition is heated in nitrogen at a temperature of from about 700° C. to about 800° C. to form the hardened molecular sieve catalyst composition. Heating is carried out for a period of time of from about 30 minutes to about 15 hours, preferably from about 1 hour to about 10 hours, more preferably from about 1 hour to about 5 hours, and most preferably from about 2 hours to about 4 hours.

III. Method of Using the Hardened Molecular Sieve Catalyst

The catalyst compositions described above are useful in a variety of processes including cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene; polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecyclization; disproportionation, of for example toluene to make benzene and paraxylene; oligomerization, of for example straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

The hardened molecular sieve catalyst of this invention is particularly useful in systems in which the catalyst is circulated throughout a reaction system. Circulation type systems that cause particular problems with attrition of circulated catalyst are those that include a reactor for carrying out the reaction, and a regenerator for intermittently regenerating the catalyst.

In one practical embodiment, the process is conducted as a fluidized bed process or high velocity fluidized bed process utilizing a reactor system, a regeneration system and a recovery system. In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent.

Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kpaa) to about 500 psia (3448 kpaa), such as from about 20 psia (138 kPaa) to about 250 psia (1724 kPaa), including from about 25 psia (172 kPaa) to about 150 psia (1034 kpaa), and conveniently from about 30 psia (207 kpaa) to about 60 psia (414 kpaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336–337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2) splitter, propylene (C3) splitter and butene (C4) splitter.

Various recovery systems useful for recovering olefin(s), such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology, 4th Edition*, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all fully herein incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, can then be used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

IV. Examples of the Hardened Molecular Sieve Catalyst

Various embodiments of this invention are described in greater detail with reference to the following examples, which are intended to illustrate specific embodiments within the overall scope of the invention as claimed.

EXAMPLE-1

A slurry containing 45 wt % solid was prepared by mixing 1,125 g of a spray dried catalyst (which contained 40% SAPO-34, 10.6% alumina, and 49.4% clay) with 875 g of deionized water using a Yamato 4000D mixer (Yamato Scientific America Inc., Orangeburg, N.Y.) for 10 minutes at 600 RPM. The slurry was then mixed using a high-shear mixer, Yamato L4RT-A (Yamato Scientific America Inc., Orangeburg, N.Y.), at 6,000 RPM for 5 minutes. The resultant final product slurry had a pH of 3.9, and density of 1.45 g/cc, measured at 25° C. The viscosity of the slurry was 2,180 centipoise at 24° C., which was measured with a Brookfield LV viscometer, using a #3 spindle at 10 RPM.

EXAMPLE-2 (COMPARATIVE)

700 g of the final product slurry produced in EXAMPLE-1 was spray dried using a Yamato DL-41 spray dryer, operating in a down spray mode, using a 1 mm atomization nozzle. Spray drying conditions were as follows: feed rate, 40 g/min; inlet temperature, 350° C.; atomization pressure, 1 bar; and carrier gas flow at 60% of full setting. Spray dried products were collected in a cyclone, and calcined in a muffle furnace at 650° C. in air for 2 hours. The calcined samples were tested for attrition resistance, and found to have an ARI of 0.59 wt %/hr. The result is shown in the Figure.

EXAMPLE-3

843.75 g of the spray dried catalyst used in EXAMPLE 1 were added to 656.25 g deionized water, and mixed at 600 RPM using a Yamato 4000D mixer (Yamato Scientific America Inc., Orangeburg, N.Y.) for 10 minutes to produce a slurry. The slurry was then mixed using a high-shear mixer, Yamato L4RT-A (Yamato Scientific America Inc., Orangeburg, N.Y.) at 6,000 RPM for 10 minutes. To this slurry, 168.5 g of SAPO-34 molecular sieve was added, then further mixing was carried out using the same procedure as outlined in EXAMPLE-1. A composition made of 81.06 g of Reheis MicroDry aluminum chlorohydrate (Reheis Chemical Inc., Berkeley Heights, N.J.) and 118.84 g of deionized water was then added, and further mixing carried out using the same protocol outlined in EXAMPLE-1. Finally, 131.57 g of kaolin clay (Engelhard USP kaolin clay, Engelhard Corporation, Iselin, N.J.) was added and further mixing carried out using the same routine as in EXAMPLE-1. This resulted in a final product slurry containing 45 wt % solids, of which 75% was spray dried product and 25% was virgin SAPO-34 molecular sieve, aluminum chlorohydrate, and clay. The final product slurry had a pH value of 4.0, measured at 25° C., and a density of 1.39 g/cc, measured at 25° C. The viscosity of the final product slurry was 3,400 centipoise at 24° C., which was measured with a Brookfield LV viscometer, using a #3 spindle at 10 RPM.

EXAMPLE-4

700 g of the final product slurry produced in EXAMPLE-3 was spray dried using a Yamato DL-41 spray dryer, operating in a down spray mode, using a 1 mm atomization nozzle. Spray drying conditions were as follows: feed rate, 40 g/min; inlet temperature, 350° C.; atomization pressure, 1 bar; and carrier gas flow at 60% of full setting. Spray dried products were collected in a cyclone, and then calcined in a muffle furnace at 650° C. in air for 2 hours. The calcined samples were tested for attrition resistance, and found to have an ARI of 0.36 wt %/hr. The result is shown in the Figure.

EXAMPLE-5

562.5 g of the spray dried catalyst used in EXAMPLE 1 was added to 437.5 g deionized water, and mixed at 600 RPM using a Yamato 4000D mixer (Yamato Scientific America Inc., Orangeburg, N.Y.) for 10 minutes to form a slurry. The slurry was then mixed using a high-shear mixer, Yamato L4RT-A (Yamato Scientific America Inc., Orangeburg, N.Y.) at 6,000 RPM for 10 minutes. To this slurry, 337.0 g of SAPO-34 molecular sieve was added, and further mixing was carried out using the same procedure as outlined in EXAMPLE-1. To that slurry was added a composition made of 162.18 g of Reheis MicroDry aluminum chlorohydrate (Reheis Chemical Inc., Berkeley Heights, N.J.) and 237.68 of deionized water. Further mixing was carried out using the same protocol outlined in EXAMPLE-1. Finally, 263.14 g of kaolin clay (Engelhard USP kaolin clay, Engelhard Corporation, Iselin, N.J.) was added and mixed using the same routine used in EXAMPLE-1. This resulted in a final product slurry containing 45 wt % solids, of which 50% came from the spray dried molecular sieve and 50% came from the combination of virgin SAPO-34 molecular sieve, aluminum chlorohydrate, and clay. The final product slurry had a pH value of 4.0, measured at 25° C., and a density of 1.38 g/cc, measured at 25° C. The viscosity of the final product slurry was 4,860 centipoise at 24° C., which was measured with a Brookfield LV viscometer, using a #3 spindle at 10 RPM.

EXAMPLE-6

700 g of the final product slurry produced in EXAMPLE-5 was spray dried using a Yamato DL-41 spray dryer, operating in a down spray mode, using a 1 mm atomization nozzle. Spray drying conditions were as follows: feed rate, 40 g/min; inlet temperature, 350° C.; atomization pressure, 1 bar; carrier gas flow at 60% of full setting. Spray dried products were collected in a cyclone, and calcined in a muffle furnace at 650° C. in air for 2 hours. The calcined samples were tested for attrition resistance, and found to have an ARI of 0.40 wt %/hr. The result is shown in the Figure.

EXAMPLE-7

281.25 g of the spray dried catalyst used in EXAMPLE 1 was added to 218.75 g deionized water, and mixed at 600 RPM using a Yamato 4000D mixer (Yamato Scientific America Inc., Orangeburg, N.Y.) for 10 minutes to form a slurry. The slurry was then mixed using a high-shear mixer, Yamato L4RT-A (Yamato Scientific America Inc., Orangeburg, N.Y.) at 6,000 RPM for 10 minutes. To this slurry, 505.0 g of SAPO-34 molecular sieve was added, and further mixing was carried out using the same procedure as outlined in EXAMPLE-1. To that slurry was added a composition made of 243.27 g of Reheis MicroDry aluminum chlorohydrate (Reheis Chemical Inc., Berkeley Heights, N.J.) and 356.52 g of deionized water. Further mixing was carried out using the same protocol outlined in EXAMPLE-1. Finally, 394.71 g of kaolin clay (Engelhard USP kaolin clay, Engelhard Corporation, Iselin, N.J.) was added and mixed using the same routine used in EXAMPLE-1. This resulted in a final product slurry containing 45 wt % solids, of which 25% came from the spray dried molecular sieve and 75% came from the combination of the virgin SAPO-34 molecular sieve, aluminum chlorohydrate, and clay. The final product slurry had a pH value of 4.0, measured at 25° C., and a density of 1.46 g/cc, measured at 25° C. The viscosity of the final product slurry was 7,610 centipoise at 24° C., which was measured with a Brookfield LV viscometer, using a #3 spindle at 10 RPM.

EXAMPLE-8

700 g of the final product slurry produced in EXAMPLE-7 was spray dried using a Yamato DL-41 spray dryer, operating in a down spray mode, using a 1 mm atomization nozzle. Spray drying conditions were: feed rate, 40 g/min; inlet temperature, 350° C.; atomization pressure, 1 bar; and carrier gas flow at 60% of full setting. Spray dried products were collected in a cyclone, and calcined in a muffle furnace at 650° C. in air for 2 hours. The calcined samples were tested for attrition resistance, and found to have an ARI of 0.25 wt %/hr. The result is shown in the Figure.

EXAMPLE-9 (COMPARATIVE)

This example is similar to that of EXAMPLES 3, 5, and 7, except that no spray dried product was contained in the final product slurry. A slurry containing 45 wt % solid (on calcined basis), 40% being SAPO-34, 10.6% $Al_2O_3$, and 49.4% clay, was prepared by adding 2,988.93 g of a SAPO-34 filtercake to 1,703.84 g of deionized water, and mixing at 1,500 RPM using a Yamato 4000D mixer (Yamato Scientific America Inc., Orangeburg, N.Y.) for 15 minutes. The slurry further mixed by a high-shear treatment using a Silverson high shear L4RT-A mixer at 6,000 RPM for 10 minutes (Slurry A). Slurry A had a pH value of 6.3, measured at 26° C. An aluminum chlorohydrate slurry was made by adding 869.03 g of Reheis MicroDry aluminum chlorohyrate (Reheis Inc., Berkeley Heights, N.J.) to 859.12 g of deionized water and mixing at 1,500 RPM using a Yamato 4000D mixer (Yamato Scientific America Inc., Orangeburg, N.Y.) for 15 minutes. This slurry was further mixed by a high-shear treatment using a Silverson high shear L4RT-A mixer at 6,000 RPM for 10 minutes to form a Slurry B, having a pH of 3.3, measured at 31° C. Slurry A, containing the SAPO-34 molecular sieve, and the Slurry B, containing the aluminum chlorohydrate, were combined and mixed at 1,500 RPM using a Yamato 4000D mixer (Yamato Scientific America Inc., Orangeburg, N.Y.) for 15 minutes. This slurry was then further mixed using a Silverson high-shear mixer at 6,000 RPM for 10 minutes, and had a pH value of 4.2, measured at 30° C. To this slurry was added 2302.3 g of kaolin clay (Engelhard ASP Ultrafine kaolin clay, Engelhard Corporation, Iselin, N.J.), and the slurry was constantly mixed at 250–400 RPM, then further mixed at 1,500 RPM using a Yamato 4000D mixer (Yamato Scientific America Inc., Orangeburg, N.Y.) for 15 minutes. This slurry was further mixed by a high-shear mixing step using a Silverson L4RT-A mixer at 6,000 RPM for 10 minutes. The solid content of this slurry was adjusted to 45% solids by adding 283.97 g of deionized water, then further mixed at 1,500 RPM for 15 minutes using the Yamato mixer. Subsequent high-shear mixing was then carried out using the Silverson mixer at 6,000 RPM for 10 minutes to form a final product mixer. This final product slurry had a pH value of 3.8, measured at 36° C. A final product slurry of 8,000 g was formed, which contained 45% solids (on calcined basis). The solids were comprised of 40% SAPO-34 molecular sieve, 10.6% alumina, and 49.4% clay. The final product slurry had a pH value of 4.34, measured at 25° C.; a density of 1.40 g/cc, measured at 23° C.; and a viscosity of 4,920 centipoise at 24° C., which was measured with a Brookfield LV viscometer, using a #3 spindle at 10 RPM.

EXAMPLE-10 (COMPARATIVE)

750 g of the final product slurry produced in EXAMPLE-9 was spray dried using a Yamato DL-41 spray dryer, operating in a down spray mode, using a 1 mm atomization nozzle. Spray drying conditions were: feed rate, 40 g/min; inlet temperature, 350° C.; atomization pressure, 1 bar; and carrier gas flow at 60% of full setting. Spray dried products were collected in a cyclone, and calcined in a muffle furnace at 650° C. in air for 2 hours. The calcined samples were tested for attrition resistance, and found to have an ARI of 0.95 wt %/hr. The result is shown in the Figure.

Having now fully described this invention, it will be appreciated by those skilled in the art that the invention can be performed within a wide range of parameters within what is claimed, without departing from the spirit and scope of the invention.

The invention claimed is:

1. A method of making a hardened molecular sieve catalyst composition, the method comprising the steps of:
   a) mixing together crystalline molecular sieve that has not been formulated into a catalyst composition, liquid, and formulated molecular sieve catalyst that contains template material and one or more of matrix material and binder to form a slurry of solids and liquid, wherein from 15 wt % to 80 wt % of the solids in the slurry, based on total weight of solids in the slurry, is the formulated molecular sieve catalyst;
   b) drying the slurry; and
   c) calcining the dried slurry to form the hardened molecular sieve catalyst composition.

2. The method of claim 1, wherein binder is included in the mixing of step a) to form the slurry.

3. The method of claim 2, wherein the binder is an inorganic oxide sol.

4. The method of claim 3, wherein the inorganic oxide sol is an alumina-containing sol.

5. The method of claim 1, wherein matrix material is included in the mixing of step a) to form the slurry.

6. The method of claim 5, wherein the matrix material is clay.

7. The method of claim 1, wherein the formulated molecular sieve catalyst is in an amount effective to form a hardened molecular sieve catalyst having an API of not greater than 0.6 wt %/hr upon calcining.

8. The method of claim 7, wherein the formulated molecular sieve catalyst is in an amount effective to form a hardened molecular sieve catalyst having an ARI of not greater than 0.5 wt %/hr upon calcining.

9. The method of claim 8, wherein the formulated molecular sieve catalyst is in an amount effective to form a hardened molecular sieve catalyst having an ARI of not greater than 0.4 wt %/hr upon calcining.

10. The method of claim 1, wherein from 20 wt % to 40 wt % of the solids in the slurry, based on total weight of solids in the slurry, is the formulated molecular sieve catalyst.

11. The method of claim 10, wherein from 20 wt % to 30 wt % of the solids in the slurry, based on total weight of solids in the slurry, is the formulated molecular sieve catalyst.

12. The method of claim 1, wherein the crystalline molecular sieve mixed in step a) is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, metal containing molecular sieves thereof, and mixtures thereof.

13. The method of claim 1, wherein the formulated molecular sieve catalyst mixed in step a) contains molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, metal containing molecular sieves thereof, and mixtures thereof.

* * * * *